(12) United States Patent
Lye et al.

(10) Patent No.: US 7,294,409 B2
(45) Date of Patent: Nov. 13, 2007

(54) MEDICAL DEVICES HAVING POROUS LAYERS AND METHODS FOR MAKING SAME

(75) Inventors: Whye-Kei Lye, Charlottesville, VA (US); Kareen Looi, Charlottesville, VA (US); Michael L. Reed, Charlottesville, VA (US)

(73) Assignee: University of Virginia, Charlottesville, NC (US)

( * ) Notice: Subject to any disclaimer, the term of this patent is extended or adjusted under 35 U.S.C. 154(b) by 365 days.

(21) Appl. No.: 10/713,244

(22) Filed: Nov. 13, 2003

(65) Prior Publication Data

US 2004/0148015 A1    Jul. 29, 2004

Related U.S. Application Data

(60) Provisional application No. 60/426,106, filed on Nov. 13, 2002.

(51) Int. Cl.
- *B22D 25/00* (2006.01)
- *A61F 2/00* (2006.01)
- *A61F 2/06* (2006.01)
- *B44C 1/22* (2006.01)

(52) U.S. Cl. .................. 428/610; 424/423; 216/75; 623/901; 623/1.39

(58) Field of Classification Search .............. 623/1.15, 623/1.39, 1.4, 1.42, 1.44, 901; 424/422–424; 428/610, 613; 427/2.24–2.27; 607/658.5; 216/75; 148/668–678
See application file for complete search history.

(56) References Cited

U.S. PATENT DOCUMENTS

| | | |
|---|---|---|
| 2,021,520 A | 11/1935 | Reichmann |
| 3,190,749 A * | 6/1965 | Fleming .................. 428/610 |
| 3,338,805 A | 8/1967 | Pochily et al. |
| 3,923,969 A | 12/1975 | Baukal et al. |

(Continued)

FOREIGN PATENT DOCUMENTS

EP    0 392 738 A1    10/1990

(Continued)

OTHER PUBLICATIONS

Forty, et al., "*A Micromorphological Study of the Dissolution of Silver-Gold Alloys in Nitric Acid*," Philosophical Magazine A, 1980, vol. 42, No. 3, 295-318.

(Continued)

*Primary Examiner*—David J. Isabella
(74) *Attorney, Agent, or Firm*—Knobbe Martens Olson & Bear LLP

(57) ABSTRACT

Methods for fabricating a medical device having at least one porous layer include providing a medical device having at least one alloy and removing at least one component of the alloy to form the porous layer. Although methods may be used to make stent devices with porous layers, any other suitable medical device may be made having one or more porous layers. An alloy may include any suitable combination of metals and sometimes a combination of metal and non-metal. In some embodiments, one or more of the most electrochemically active component(s) of an alloy are removed by the dissolving (or "dealloying") process, to leave a porous matrix behind. The porous matrix layer may then be infused with one or more therapeutic agents for enhancing treatment of a patient.

69 Claims, 3 Drawing Sheets

U.S. PATENT DOCUMENTS

| | | | |
|---|---|---|---|
| 3,948,254 A | | 4/1976 | Zaffaroni |
| 3,993,072 A | | 11/1976 | Zaffaroni |
| 4,218,255 A | | 8/1980 | Bajpai et al. |
| 4,459,252 A | * | 7/1984 | MacGregor ............. 264/46.9 |
| 4,977,038 A | * | 12/1990 | Sieradzki et al. .......... 428/610 |
| 5,246,689 A | | 9/1993 | Beck et al. |
| 5,340,614 A | | 8/1994 | Perman et al. |
| 5,508,060 A | | 4/1996 | Perman et al. |
| 5,569,198 A | * | 10/1996 | Racchini ............. 604/103.01 |
| 5,769,884 A | | 6/1998 | Solovay |
| 5,843,172 A | | 12/1998 | Yan |
| 5,843,289 A | | 12/1998 | Lee et al. |
| 5,947,893 A | | 9/1999 | Agrawal et al. |
| 5,972,027 A | | 10/1999 | Johnson |
| 5,980,551 A | * | 11/1999 | Summers et al. .......... 606/194 |
| 5,985,307 A | * | 11/1999 | Hanson et al. ............. 424/423 |
| 6,019,784 A | | 2/2000 | Hines |
| 6,027,863 A | | 2/2000 | Donadio, III |
| 6,093,498 A | * | 7/2000 | Baldi ..................... 428/570 |
| 6,107,004 A | | 8/2000 | Donadio, III |
| 6,183,255 B1 | | 2/2001 | Oshida |
| 6,203,732 B1 | | 3/2001 | Clubb et al. |
| 6,240,616 B1 | | 6/2001 | Yan |
| 6,273,913 B1 | | 8/2001 | Wright et al. |
| 6,379,381 B1 | | 4/2002 | Hossainy et al. |
| 6,506,437 B1 | | 1/2003 | Harish et al. |
| 6,527,938 B2 | | 3/2003 | Bales et al. |
| 6,709,379 B1 | | 3/2004 | Brandau et al. |
| 6,712,845 B2 | | 3/2004 | Hossainy |
| 6,758,859 B1 | * | 7/2004 | Dang et al. ............. 623/1.15 |
| 6,797,311 B2 | | 9/2004 | Loomis et al. |
| 6,805,898 B1 | | 10/2004 | Wu et al. |
| 6,939,376 B2 | | 9/2005 | Shulze et al. |
| 2002/0052650 A1 | | 5/2002 | Rourke et al. |
| 2002/0133224 A1 | | 9/2002 | Bajgar et al. |
| 2002/0198601 A1 | | 12/2002 | Bales et al. |
| 2003/0060873 A1 | | 3/2003 | Gertner et al. |
| 2003/0186522 A1 | | 10/2003 | Duan et al. |
| 2004/0000046 A1 | | 1/2004 | Stinson |
| 2004/0005723 A1 | | 1/2004 | Empedocles et al. |
| 2004/0026684 A1 | | 2/2004 | Empedocles |
| 2004/0039438 A1 | | 2/2004 | Alt |
| 2004/0073298 A1 | | 4/2004 | Hossainy |
| 2004/0095658 A1 | | 5/2004 | Buretea et al. |
| 2004/0118448 A1 | | 6/2004 | Scher et al. |
| 2004/0136866 A1 | | 7/2004 | Pontis et al. |
| 2004/0146560 A1 | | 7/2004 | Whiteford et al. |
| 2004/0148015 A1 | | 7/2004 | Lye et al. |
| 2005/0079200 A1 | | 4/2005 | Rathenow et al. |
| 2005/0106212 A1 | * | 5/2005 | Gertner et al. ............. 424/425 |

FOREIGN PATENT DOCUMENTS

| | | |
|---|---|---|
| EP | 0 706 376 B1 | 4/1996 |
| EP | 1 319 416 A1 | 6/2003 |
| WO | WO 00/01322 | 1/2000 |
| WO | WO 00/25841 | 5/2000 |
| WO | WO 00/48660 | 8/2000 |
| WO | WO 03/045582 A1 | 6/2003 |

OTHER PUBLICATIONS

Martinez, et al., "*Kinetics of the Dissolution of Pure Silver and Silver-Gold Alloys in Nitric Acid Solution*," Metallurigical Transactions B, vol. 24B, pp. 827-837 (plus cover sheet), Oct. 1993.

Li, et al., "*Ductile-Brittle Transition in Random Porous Au*," Physical Review Letters, vol. 68, No. 8, pp. 1168-1171, Feb. 24, 1992.

Ateya, et al., "*The Effects of Potential and Kinetic Parameters on the Formation of Passivating Nobel Metal Rich Surface Layers During the Selective Dissolution of Binary Alloys*," Corrosion Science, vol. 38, No. 8, pp. 1245-1267, 1996.

Eriebacher, et al., "*Evolution of Nanoporosity in Dealloying*," Nature, vol. 410, pp. 450-452, Mar. 22, 2001.

Simmonds, et al., "*The Observation of a Threshold in the De-Alloying of Sputter-Deposited $Pt_xAl_{1-x}$ Alloy Thin Films*," Corrosion Science, vol. 40, No. 1, pp. 43-48, 1998.

Tulimieri, et al., "*Ordering of Helium Mixtures in Porous Gold*," Phys. Rev. Lett., vol. 82, No. 1, pp. 121-124, Jan. 4, 1999.

Li, et al., "*Synthesis of Porous Ni-Ti Shape-Memory Alloys by Self-Propagating High-Terperature Synthesis: Reaction Mechanism and Anisotropy in Pore Structure*," Acta Mater., 48 pp. 3895-3904, 2000.

Pugh, et al., "*Formation of Nanoporous Platinum by Selective Dissolution of Cu from $Cu_{0.75}Pt_{0.25}$*," J. Mater. Res., vol. 18, No. 1, Jan. 2003.

Newman, et al., "*Alloy Corrosion*," MRS Bulletin 74 (7), Jul. 24, 1999.

M. Grimwade, "*The Surface Enrichment of Carat Gold Alloys—Depletion Gilding*," Gold Technology, Issue 26, pp. 16-23, Jul. 1999.

Gertner, et al., "*Drug Delivery from Electrochemically Deposited Thin Metal Films*," Electrochemical and Solid-State Letters, 6 (4), pp. J4-J6, 2003.

Stein, et al., "*Dealloying Studies with Electrodeposited Zinc-Nickel Alloy Films*," Electrochimica Acta, vol. 43, Nos. 1-2, pp. 223-226, 1998.

Schroers, et al., "*Amorphous Metallic Foam*," Applied Physics Letters, vol. 82, No. 3. pp. 370-372, Jan. 20, 2003.

Wieneke, et al., "*Synergistic Effects of a Novel Nanoporous Stent Coating and Tacrolimus on Intima Proliferation in Rabbbits*," Catheterization and Cardiovascular Interventions, 60:pp. 399-407, 2003.

Ji, et al., "*Fabrication of Nanoporous Gold Nanowires*," Applied Physics Letters, vol. 81, No. 23, pp. 4437-4439. Dec. 2, 2002.

Kazeminezhad, et al., "*Alloys by Precision Electrodeposition*," Applied Physics Letters, vol. 78, No. 7, pp. 1014-1016, Feb. 12, 2001.

Sieradzki, et al., "*The Dealloying Critical Potential*," Journal of The Electrochemical Society, 149 (8), pp. B370-B377, 2002.

Itokazu, et al., "*Local Drug Delivery System Using Ceramics: Vacuum Method for Impregnating a Chemoterapeutic Agent into a Porous Hydroxyapatite Block*," Journal of Material Science: Materials of Medicine, vol. 10, No. 4, pp. 249-252, Apr. 1999.

Translation of Korean Office Action dated Aug. 29, 2006.

* cited by examiner

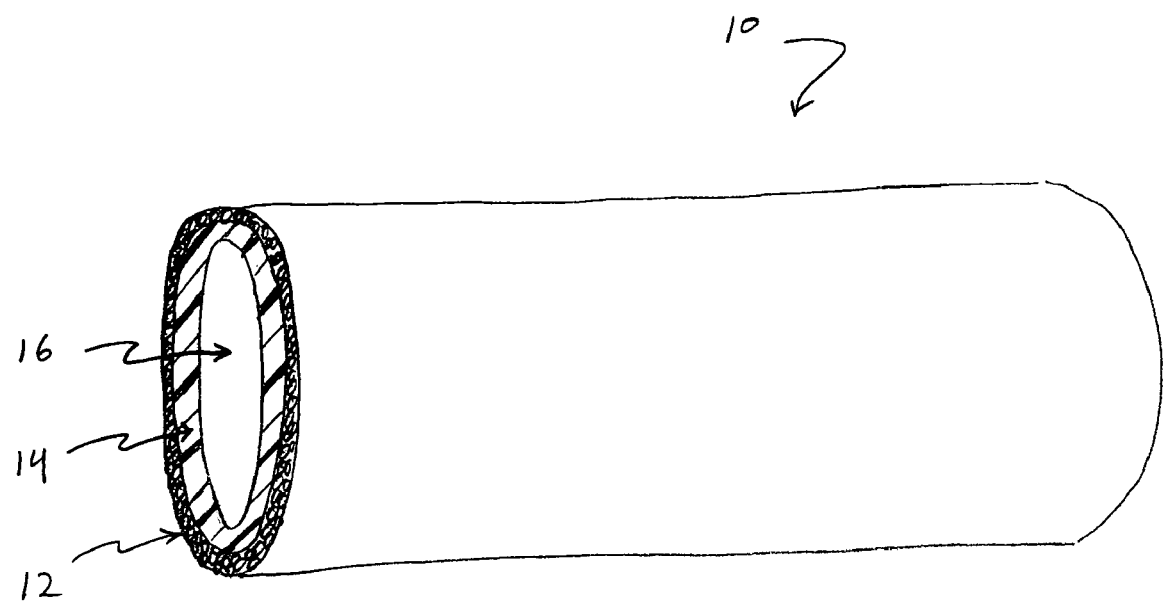
FIG_1

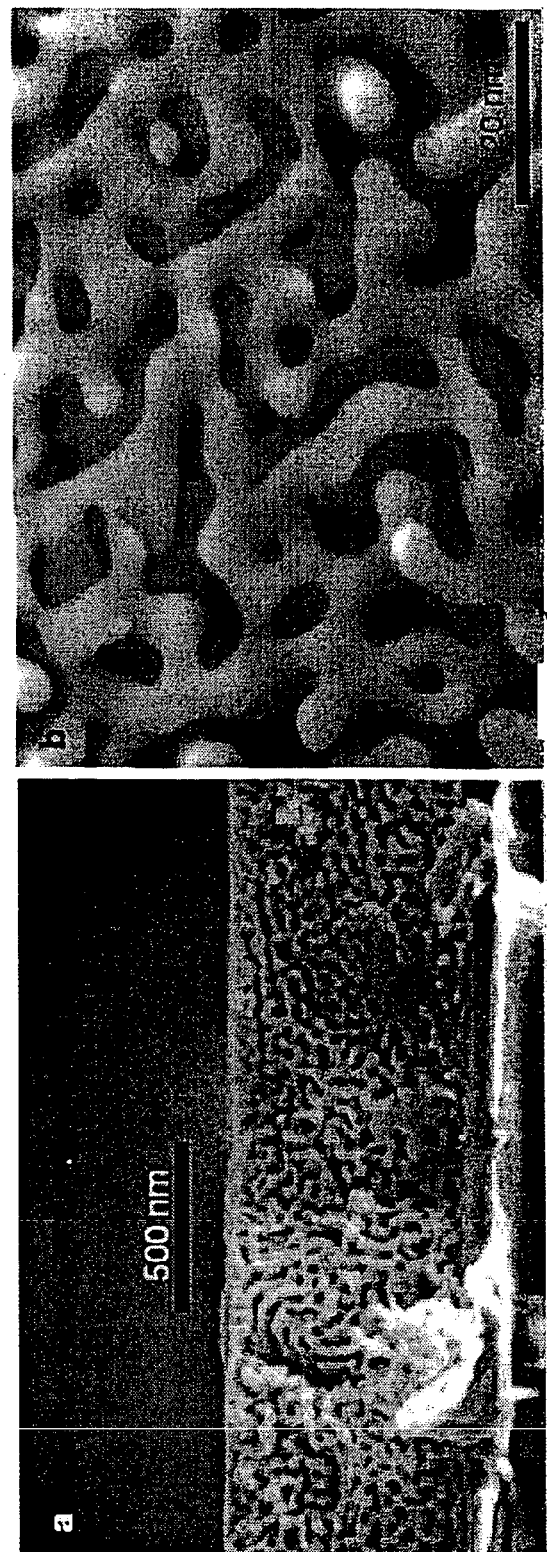
FIG_2B
FIG_2A

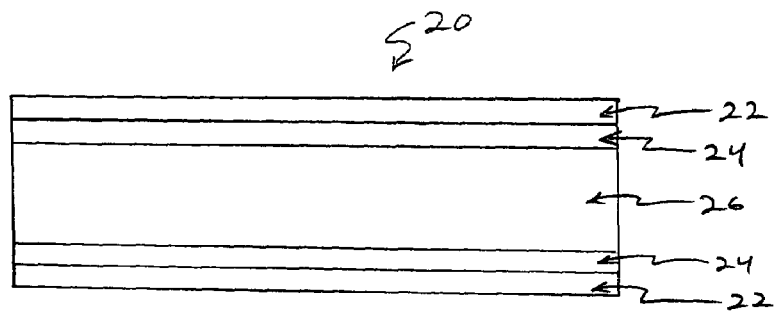
FIG_3A
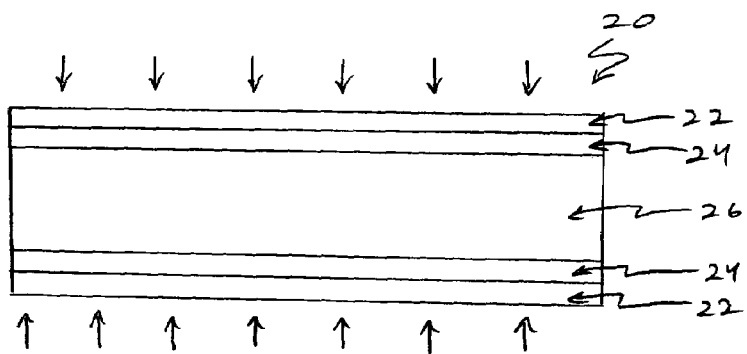
FIG_3B
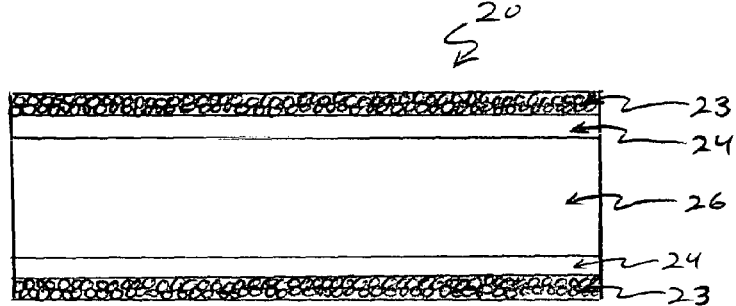
FIG_3C

MEDICAL DEVICES HAVING POROUS LAYERS AND METHODS FOR MAKING SAME

BACKGROUND OF THE INVENTION

The present invention relates generally to medical devices and methods for making same. More specifically, the invention relates to implantable medical devices having at least one porous layer, and methods for making such devices.

Implantable medical devices are increasingly being used to deliver one or more therapeutic agents to a site within a body. Such agents may provide their own benefits to treatment and/or may enhance the efficacy of the implantable device. For example, much research has been conducted into the use of drug eluting stents for use in percutaneous transluminal coronary angioplasty (PTCA) procedures. Although some implantable devices are simply coated with one or more therapeutic agents, other devices include means for containing, attaching or otherwise holding therapeutic agents to provide the agents at a treatment location over a longer duration, in a controlled-release manner, or the like.

Porous materials, for example, are commonly used in medical implants as matrices for the retention of therapeutic agents. Materials that have been used for this purpose include ceramics such as hydroxyapatites and porous alumina, as well as sintered metal powders. Polymeric materials such as poly(ethylene glycol)/poly(L-lactic acid) (PLGA) have also been used for this purpose. These materials are typically applied as coatings to the medical implant, raising issues regarding coating adhesion, mechanical properties, and material biocompatibility. Further, application of these coatings introduces additional complexity to the fabrication process, increasing overall production costs.

Therefore, it would be advantageous to have improved implantable medical devices with porous layers and methods for fabricating those devices. Such methods would ideally produce a more adherent and mechanically robust porous layer while simplifying device manufacture. Methods would also ideally provide porous layers having desired pore sizes and densities. At least some of these objectives will be met by the present invention.

BRIEF SUMMARY OF THE INVENTION

Methods of the present invention provide means for fabricating an implantable medical device having at least one porous layer. In one aspect, a method of fabricating an implantable medical device having a porous layer for releasably containing at least one therapeutic agent includes providing an implantable medical device comprising at least one alloy and removing at least one component of the alloy to form the porous layer. In some embodiments, the component is removed to form the porous layer as a biocompatible material, such as gold. In some embodiments, the medical device comprises a tubular stent device having an outer surface and an inner surface. For example, the stent device may comprise a coronary artery stent for use in a percutaneous transluminal coronary angioplasty (PTCA) procedure. In some of these embodiments, the alloy is disposed along the outer surface of the stent device.

Optionally, providing the implantable medical device may also include depositing the alloy on at least one surface of the medical device. In various embodiments, the alloy may be disposed along an outer surface of the implantable medical device, such that the dissolving step forms the porous layer on the outer surface of the device. In some embodiments, the alloy includes one or more metals, such as but not limited to gold, silver, nitinol, steel, chromium, iron, nickel, copper, aluminum, titanium, tantalum, cobalt, tungsten, palladium, vanadium, platinum and/or niobium. In other embodiments, the alloy comprises at least one metal and at least one non-metal. Optionally, before the dissolving step at least one substance may be embedded within the alloy. For example, a salt or an oxide particle may be embedded in the alloy to enhance pore formation upon dissolution.

Dissolving one or more components of the alloy may involve exposing the alloy to a dissolving substance. For example, a stainless steel alloy may be exposed to sodium hydroxide in one embodiment. Typically, one or more of the most electrochemically active components of the alloy are dissolved. After the dissolving step, additional processing may be performed. For example, the device may be coated after the dissolving step with titanium, gold and/or platinum. Some embodiments further include introducing at least one therapeutic agent into the porous layer. For example, the therapeutic agent may be introduced by liquid immersion, vacuum dessication, high pressure infusion or vapor loading in various embodiments. The therapeutic agent may be any suitable agent or combination of agents, such as but not limited to anti-restenotic agent(s) or anti-inflammatory agent (s), such as Rapamycin, Sirolimus, Taxol, Prednisone, and/or the like. In other embodiments, live cells may be encapsulated by the porous layer, thereby allowing transport of selected molecules, such as oxygen, glucose, or insulin, to and from the cells, while shielding the cells from the immune system of the patient. Some embodiments may optionally include multiple porous layers having various porosities and atomic compositions.

In another aspect, a method for treating a blood vessel using an implantable medical device having a porous layer for releasably containing at least one therapeutic agent includes: providing at least one implantable stent having a porous layer for releasably containing at least one therapeutic agent; and placing the stent within the blood vessel at a desired location, wherein the stent releases the at least one therapeutic agent from the porous layer after placement. For example, in one embodiment the desired location may comprise an area of stenosis in the blood vessel, and the at least one therapeutic agent may inhibit re-stenosis of the blood vessel. Again, the therapeutic agent in some embodiments may be one or more anti-restenosis agents, anti-inflammatory agents, or a combination of both. In one embodiment, the blood vessel may be a coronary artery. In such embodiments, the placing step may involve placing the stent so as to contact the porous layer with at least one of a stenotic plaque in the blood vessel and an inner wall of the blood vessel.

In still another aspect, an implantable medical device has at least one porous layer comprising at least one remaining alloy component and interstitial spaces, wherein the interstitial spaces comprise at least one removed alloy component space of an alloy, the alloy comprising the at least one remaining alloy component and the at least one removed alloy component. In some embodiments, the porous layer comprises a matrix. Also in some embodiments, the implantable medical device comprises an implantable stent device having an outer surface and an inner surface, and the porous layer is disposed along the outer surface. For example, the stent device may comprise a coronary artery stent for use in a percutaneous transluminal coronary angioplasty procedure. As described above, the alloy may comprise one or more metals selected from the group consisting of gold, silver, nitinol, steel, chromium, iron, nickel, copper, aluminum, titanium, tantalum, cobalt, tungsten, palladium, vanadium, platinum and/or niobium. For example, the alloy may comprise stainless steel and the porous layer may comprise iron and nickel.

In some embodiments, the component (or components) that is dissolved comprises a most electrochemically active component of the alloy. Generally, the device further includes at least one therapeutic agent disposed within the at least one porous layer. Any such agent or combination of agents is contemplated. Finally, the device may include a titanium or platinum coating over an outer surface of the device.

BRIEF DESCRIPTION OF THE DRAWINGS

FIG. 1 is a perspective view of an implantable stent device having a porous layer according to one embodiment of the present invention.

FIGS. 2A-2B are electron micrographs of a porous layer formed by dissolving silver from a gold-silver alloy, according to one embodiment of the present invention.

FIGS. 3A-3C are cross-sectional side views showing a method of making an implantable stent device having a porous layer, according to one embodiment of the present invention.

DETAILED DESCRIPTION OF THE INVENTION

Methods of the present invention provide means for fabricating an implantable medical device having at least one porous layer. Generally, the methods involve providing an implantable medical device containing an alloy and removing at least one component of the alloy to form the porous layer. In some embodiments, an alloy may first be deposited on an implantable device and one or more components of the alloy may then be removed to form the porous layer. Such methods are often referred to as "dealloying." For a general description of dealloying methods, reference may be made to "Evolution of nanoporosity in dealloying," Jonah Erlebacher et al., Nature 410, pp. 450-453, March 2001, the entire contents of which are hereby incorporated by reference. Dealloying a layer of an implantable device provides a porous layer, which may then be infused with one or more therapeutic agents for providing delivery of an agent into a patient via the device. Use of dealloying methods will typically provide more adherent and mechanically robust porous layers on medical implantables than are currently available, while also simplifying device manufacture.

Although the following description often focuses on the example of implantable stent devices for use in PTCA procedures, any suitable implantable medical device may be fabricated with methods of the invention. Other devices may include, but are not limited to, other stents, stent-grafts, implantable leads, infusion pumps, vascular access devices such as implantable ports, orthopedic implants, implantable electrodes, and the like. Similarly, devices fabricated via methods of the present invention may be used to deliver any suitable therapy or combination of therapies in a patient care context, veterinary context, research setting or the like. Therapeutic agents may include, for example, drugs, genes, anti-restenosis agents, anti-thrombogenic agents, antibiotic agents, anti-clotting agents, anti-inflammatory agents, cancer therapy agents and/or the like. Thus, the following description of specific embodiments is provided for exemplary purposes only and should not be interpreted to limit the scope of the invention as set forth in the appended claims.

Referring now to FIG. 1, an implantable medical device fabricated by methods of the present invention may include an elongate stent device 10, having two or more layers 12, 14 and a lumen 16. In one embodiment, stent device 10 includes an outer porous layer 12 and an inner non-porous layer 14. Other embodiments may suitably include an inner porous layer 12 and an outer non-porous layer 14, multiple porous layers 12, multiple non-porous layers 14, a porous coating over an entire surface of a medical device, or any combination of porous and non-porous surfaces, layers, areas or the like to provide a desired effect. In one embodiment, for example, multiple porous layers may be layered over one another, with each layer having a different porosity and atomic composition. Porous layer 12 and non-porous layer 14 may have any suitable thicknesses in various embodiments. In some embodiments, for example, a very thin porous layer 12 may be desired, such as for delivery of a comparatively small amount of therapeutic agent. In another embodiment, a thicker porous layer 12 may be used for delivery of a larger quantity of therapeutic agent and/or for a longer duration of agent delivery. Any suitable combination and configuration of porous layer 12 and non-porous layer 14 is contemplated. In one embodiment, porous layer 12 may comprise the entire thickness of stent device 10, so that the device is completely porous. Again, stent device 10 is only one example of a device with which porous layers may be used. Other devices may not have a lumen, for example, but may still be suitable for use in the present invention.

As mentioned above, any medical device may be fabricated with one or more porous layers 12 according to embodiments of the present invention. Where the device is an implantable stent device 10, any suitable type, size and configuration of stent device may be fabricated with one or more porous layers 12. In one embodiment, stent device 10 comprises an expandable stent for implantation in a coronary artery during a PTCA procedure. Such a stent device 10 may be fabricated from any suitable material or combination of materials. In one embodiment, stent device 10 comprises a stainless steel non-porous layer 14 arid an iron and nickel porous layer 12. In some embodiments, porous layer 12 may be formed of a biocompatible material, such as gold. In other embodiments, porous layer 12 may be formed from a cobalt-chromium alloy such as L605. Any other suitable material or combination of materials is contemplated. Furthermore, stent device 10 may include a layer or coating comprising a biocompatible material such as titanium, gold or platinum, which may provide biocompatibility, corrosion resistance or both.

With reference now to FIGS. 2A and 2B, a porous layer 12 is shown in greater detail. Porous layer 12 in these figures was made by selectively dissolving silver from a gold-silver alloy. As can be seen from the scanning electron micrographs, porous layer 12 comprises a matrix of pores and structural elements. In any given embodiment, the size and density of such pores may be varied by varying one or more elements of a method for making the device and forming porous layer 12. For example, one or more components of an alloy, a substance used to selectively dissolve the alloy, duration time of exposing the alloy to the dissolving substance, or the like may be chosen to give porous layer 12 certain desired characteristics. Thermal anneals prior or subsequent to the dealloying process may also be performed to vary pore size and density. Any suitable combination of porous layer thickness, pore size, pore density and the like is contemplated within the scope of the present invention.

Although not shown in FIGS. 1 and 2, any implantable medical device of the present invention may include one or more therapeutic agents disposed within one or more porous layers 12. As discussed above, any agent or combination of agents may be included. Additionally, as described further below, any suitable method for introducing an agent into a porous layer may be used.

Referring now to FIGS. 3A through 3C, a method for fabricating an implantable medical device 20 having a porous layer suitably includes providing an implantable device comprising at least one alloy and removing at least one component of the alloy to form the porous layer. As shown in the cross-sectional FIG. 3A, a medical device 20 such as a stent may include a precursor alloy layer 22, a substrate layer 24 and a lumen. Precursor alloy layer 22 can be deposited onto substrate layer 24 by various processes, including but not limited to physical vapor deposition, ion implantation, sputter deposition, thermal or electron beam evaporation, chemical vapor deposition, pulsed laser deposition, or the like. Using such techniques, precursor alloy layer 22 may be synthesized in situ from various materials, as described previously, such that exposure to the dealloying process will remove the sacrificial component of precursor alloy layer 22, leaving behind a porous matrix. In another embodiment, precursor alloy layer 22 and substrate layer 24 may be made from the same material. As previously described, medical device 20 may comprise any suitable stent or other device and precursor alloy layer 22, substrate layer 24 and/or other layers may be given any suitable configurations, thicknesses and the like. In some embodiments, precursor alloy layer 22 is disposed along an outer surface of device 20, while in others precursor alloy layer 22 may be disposed along an inner surface, both inner and outer surfaces, or the like. The alloy used to form precursor alloy layer 22 may comprise any suitable alloy and may be a metal-metal alloy or a metal-non-metal alloy. In various embodiments, for example, components of precursor alloy layer 22 may include steel, nitinol, chromium, brass, copper, iron, nickel, aluminum, titanium, gold, silver, tantalum, cobalt, tungsten, palladium, vanadium, platinum and/or niobium. In some embodiments, one or more additional substances may be embedded within precursor alloy layer 22 to cause or enhance pore formation during the fabrication process. For example, a salt, an oxide particle or the like may be added to precursor alloy layer 22 to enhance pore formation.

As shown in FIG. 3B, implantable medical device 20 is typically exposed to a substance (arrows) to dissolve or otherwise remove at least one component of the alloy to form the porous layer from precursor alloy layer 22. In various embodiments, any suitable substance may be used for removing at least one component of the alloy. In one embodiment, for example, the alloy comprises stainless steel, such as 316L stainless steel, and dissolving at least one component of the steel comprises exposing the steel to hot sodium hydroxide to dissolve chromium and leave iron and nickel as the porous layer. In another embodiment, a silver-gold alloy may be exposed to nitric acid to dissolve the silver and leave the gold as the porous layer (as shown in FIGS. 2A and 2B). In another embodiment, a cobalt-chromium alloy, such as L605, is modified by the addition of a sacrificial material such as silver, copper or aluminum, which is subsequently removed by processing in an appropriate solvent, such as nitric acid, sulphuric acid or phosphoric acid, to leave a porous film of the original cobal-chromium alloy.

In another embodiment, a platinum-copper alloy is dealloyed in the presence of sulphuric acid to produce porous platinum. In some embodiments, nitinol may be dissolved by a suitable dissolving substance to leave a porous layer. The dissolving process may include the use of electrochemical cells to bias device 20 in solution so as to facilitate the dealloying process. Any other suitable combination of alloy and dissolving or component-removing substance is contemplated. Furthermore, any means for exposing medical device 20 to a dissolving substance is contemplated. For example, medical device 20 may be immersed in, sprayed with, coated with, etc. any suitable substance or combination of substances.

As shown in FIG. 3C, one or more components of precursor alloy layer 22 are selectively removed to form a porous layer 23. In some embodiments, removing at least one component of the alloy comprises dissolving one or more of the most electrochemically active components of the alloy. For example, in a steel alloy the chromium component may be dissolved, leaving the iron and nickel components. Additional processing of medical device 20 may include introduction of one or more therapeutic agents into porous layer 23. Any suitable agent(s) may be introduced and they may be introduced by any desired method. For example, methods for introducing therapeutic agents include, but are not limited to, liquid immersion, vacuum dessication, high pressure infusion, vapor loading, and the like.

In another embodiment, multiple therapeutic agents may be introduced into a porous matrix composed of a plurality of porous layer 23. As described previously, the plurality of porous layers may vary in atomic composition, as well as in pore size and density. Compositional variations may allow for preferential binding to occur between the therapeutic agent and the coating, changing the elution kinetics of the agent. Pore size and density will also affect the transport kinetics of therapeutics from and across each layer. The use of a plurality of porous layers may thus allow for controlling elution kinetics of multiple therapeutic agents. In a further embodiment, live cells may be encapsulated within lumen 26 of device 20. In one such embodiment, the entire device may be made porous (such that the internal lumen and the exterior of the device are separated by a porous layer). Live cells (such a pancreatic islet cells) can be encapsulated within the internal lumen, and the porosity of the layer adjusted to allow transport of selected molecules (such as oxygen, glucose; as well as therapeutic cellular products, such as insulin, interferon), while preventing access of antibodies and other immune system agents that may otherwise attack or compromise the encapsulated cells. In some embodiments, a protective layer or coating may be formed or added to medical device 20, such as a titanium, gold or platinum layer or coating. If there is a concern that porous layer 23 may not be biocompatible, a passivation layer may be deposited into porous layer 23 to enhance biocompatibility. For instance, a very thin layer of gold may be electroplated into the dealloyed porous layer 23. Electroless deposition may also be used to achieve the same effect. Depending on the composition of porous layer 23, the porous coating may also be passivated chemically or in a reactive ion plasma.

Although the present invention has been described in full, in relation to various exemplary embodiments, various additional embodiments and alterations to the described embodiments are contemplated within the scope of the invention.

Thus, no part of the foregoing description should be interpreted to limit the scope of the invention as set forth in the following claims.

What is claimed is:

1. A method of fabricating an implantable medical device having at least one porous layer for releasably containing at least one therapeutic agent, the method comprising:
   providing an implantable medical device comprising an alloy, the alloy including a sacrificial component and a structural component; and
   selectively removing at least some of the sacrificial component of the alloy, leaving behind the structural component in the form of a matrix with tortuous pathways resulting from the removal of the sacrificial component, to form a porous layer;
   wherein the alloy is a cobalt-chromium alloy.

2. A method as in claim 1, wherein providing the implantable medical device comprises providing a tubular stent having an outer surface and an inner surface.

3. A method as in claim 2, wherein the tubular stent comprises a coronary artery stent.

4. A method as in claim 2, wherein the alloy is deposited onto the outer surface of the tubular stent.

5. A method as in claim 1, wherein the alloy is deposited on a surface of the implantable medical device.

6. A method as in claim 1, further comprising embedding at least one substance within the alloy before the removing step.

7. A method as in claim 6, wherein the at least one substance is selected from the group consisting of a salt and silicon dioxide particles.

8. A method as in claim 1, wherein selectively removing at least some of the sacrificial component comprises removing a most electrochemically active component of the alloy.

9. A method as in claim 1, further comprising introducing a therapeutic agent into the tortuous pathways of the matrix.

10. A method as in claim 9, wherein introducing the therapeutic agent comprises introducing the therapeutic agent by at least one of liquid immersion and vacuum dessication.

11. A method as in claim 9, wherein the therapeutic agent comprises at least one anti-restenosis agent or anti-inflammatory agent for inhibiting restenosis of a coronary artery.

12. A method as in claim 1, wherein the device is provided with multiple layers of alloy and multiple components are removed to provide a device having multiple porous layers.

13. A method as in claim 12, wherein the multiple porous layers have different porosities and different atomic compositions.

14. A method as in claim 4, wherein the alloy is located on the inner surface of the tubular stent.

15. A method as in claim 1, wherein the porous layer is a nanoporous layer.

16. A method as in claim 15, wherein selectively removing at least some of the sacrificial component of the alloy comprises a dealloying process.

17. a method as in claim 1, wherein the cobalt-chromium alloy is L605.

18. A method as in claim 1, further comprising:
   providing a second alloy on the implantable medical device, wherein the second alloy includes a second sacrificial component and a second structural component; and
   selectively removing at least some of the second sacrificial component of the second alloy, leaving behind the second structural component in the form of a second matrix with tortuous pathways resulting from the removal of the second sacrificial component, to form a second porous layer.

19. A method as in claim 18, wherein the second alloy is deposited on the porous layer.

20. A method as in claim 18, wherein the second alloy has a different atomic composition from the alloy.

21. A method as in claim 18, wherein the second porous layer has a different porosity from the porous layer.

22. A method as in claim 4, wherein the alloy is deposited onto the inner and outer surfaces of the tubular stent.

23. A method of fabricating an implantable medical device having at least one porous layer for releasably containing at least one therapeutic agent, the method comprising:
   providing an implantable medical device comprising an alloy, the alloy including a sacrificial component and a structural component; and
   selectively removing at least some of the sacrificial component of the alloy, leaving behind the structural component in the form of a matrix with tortuous pathways resulting from the removal of the sacrificial component, to form at least a first porous layer and a second porous layer;
   wherein the first porous layer has a different porosity and different atomic composition than the second porous layer.

24. A method as in claim 23, wherein providing the implantable medical device comprises providing a tubular stent having an outer surface and an inner surface.

25. A method as in claim 24, wherein the tubular stent comprises a coronary artery stent.

26. A method as in claim 24, wherein the alloy is deposited onto the outer surface of the tubular stent.

27. A method as in claim 23, wherein alloy is deposited on a surface of the implantable medical device.

28. A method as in claim 23, wherein the alloy comprises at least one metal selected from the group consisting of gold, silver, nitinol, steel, chromium, iron, nickel, copper, aluminum, titanium, tantalum, cobalt, tungsten, palladium, vanadium, platinum and niobium.

29. A method as in claim 23, further comprising embedding at least one substance within the alloy before the removing step.

30. A method as in claim 29, wherein the at least one substance is selected from the group consisting of a salt and silicon dioxide particles.

31. A method as in claim 23, wherein selectively removing at least some of the sacrificial component comprises removing a most electrochemically active component of the alloy.

32. A method as in claim 23, further comprising introducing a therapeutic agent into the tortuous pathways of the matrix.

33. A method as in claim 32, wherein introducing the therapeutic agent comprises introducing the therapeutic agent by at least one of liquid immersion and vacuum dessication.

34. A method as in claim 32, wherein the therapeutic agent comprises at least one anti-restenosis agent or anti-inflammatory agent for inhibiting restenosis of a coronary artery.

35. A method as in claim 26, wherein the alloy is located on the inner surface of the tubular stent.

36. A method as in claim 23, wherein the porous layer is a nanoporous layer.

37. A method as in claim 36, wherein selectively removing at least some of the sacrificial component of the alloy comprises a dealloying process.

38. A method as in claim 23, wherein the alloy is a cobalt-chromium alloy.

39. a method as in claim 38, wherein the cobalt-chromium alloy is L605.

40. A method as in claim 23, wherein the alloy comprises a silver-gold alloy.

41. A method as in claim 23, wherein the alloy comprises a stainless steel alloy.

42. A method as in claim 41, wherein the stainless steel alloy is 316L stainless steel.

43. A method as in claim 23, wherein the alloy comprises a nickel-titanium alloy.

44. A method as in claim 26, wherein the alloy is deposited onto the inner and outer surfaces of the tubular stent.

45. A method of fabricating an implantable medical device having at least one porous layer for releasably containing at least one therapeutic agent, the method comprising:
   providing an implantable medical device comprising an alloy, the alloy including a sacrificial component and a structural component; and
   selectively removing at least some of the sacrificial component of the alloy, leaving behind the structural component in the form of a matrix with tortuous pathways resulting from the removal of the sacrificial component, to form a porous layer;
   providing a second alloy on the implantable medical device, wherein the second alloy includes a second sacrificial component and a second structural component; and
   selectively removing at least some of the second sacrificial component of the second alloy, leaving behind the second structural component in the form of a second matrix with tortuous pathways resulting from the removal of the second sacrificial component, to form a second porous layer.

46. A method as in claim 45, wherein providing the implantable medical device comprises providing a tubular stent having an outer surface and an inner surface.

47. A method as in claim 46, wherein the tubular stent comprises a coronary artery stent.

48. A method as in claim 46, wherein the alloy is deposited onto the outer surface of the tubular stent.

49. A method as in claim 45, wherein alloy is deposited on a surface of the implantable medical device.

50. A method as in claim 45, wherein the alloy comprises at least one metal selected from the group consisting of gold, silver, nitinol, steel, chromium, iron, nickel, copper, aluminum, titanium, tantalum, cobalt, tungsten, palladium, vanadium, platinum and niobium.

51. A method as in claim 45, further comprising embedding at least one substance within the alloy before the removing step.

52. A method as in claim 51, wherein the at least one substance is selected from the group consisting of a salt and silicon dioxide particles.

53. A method as in claim 45, wherein selectively removing at least some of the sacrificial component comprises removing a most electrochemically active component of the alloy.

54. A method as in claim 45, further comprising introducing a therapeutic agent into the tortuous pathways of the matrix.

55. A method as in claim 54, wherein introducing the therapeutic agent comprises introducing the therapeutic agent by at least one of liquid immersion and vacuum dessication.

56. A method as in claim 54, wherein the therapeutic agent comprises at least one anti-restenosis agent or anti-inflammatory agent for inhibiting restenosis of a coronary artery.

57. A method as in claim 48, wherein the alloy is located on the inner surface of the tubular stent.

58. A method as in claim 45, wherein the first porous layer is a nanoporous layer.

59. A method as in claim 58, wherein selectively removing at least some of the sacrificial component of the alloy comprises a dealloying process.

60. A method as in claim 45, wherein the alloy is a cobalt-chromium alloy.

61. a method as in claim 60, wherein the cobalt-chromium alloy is L605.

62. A method as in claim 45, wherein the alloy comprises a silver-gold alloy.

63. A method as in claim 45, wherein the alloy comprises a stainless steel alloy.

64. A method as in claim 63, wherein the stainless steel alloy is 316L stainless steel.

65. A method as in claim 45, wherein the alloy comprises a nickel-titanium alloy.

66. A method as in claim 45, wherein the second alloy is deposited on the porous layer.

67. A method as in claim 45, wherein the second alloy has a different atomic composition from the alloy.

68. A method as in claim 45, wherein the second porous layer has a different porosity from the porous layer.

69. A method as in claim 48, wherein the alloy is deposited onto the inner and outer surfaces of the tubular stent.

* * * * *